United States Patent [19]

Bryan

[11] 4,034,099
[45] July 5, 1977

[54] COMPOSITIONS AND METHOD FOR TREATING MASTITIS IN MILK ANIMALS

[75] Inventor: Jack T. Bryan, Kalamazoo, Mich.

[73] Assignee: The Upjohn Company, Kalamazoo, Mich.

[22] Filed: Sept. 2, 1975

[21] Appl. No.: 609,462

Related U.S. Application Data

[63] Continuation-in-part of Ser. No. 456,030, March 29, 1974, abandoned.

[52] U.S. Cl. .............................. 424/271; 424/181; 424/365
[51] Int. Cl.² ................ A61K 31/43; A61K 47/00
[58] Field of Search ............ 424/365, 181, 271

[56] References Cited

UNITED STATES PATENTS

| | | | |
|---|---|---|---|
| 3,049,473 | 8/1962 | Beatson et al. | 424/365 |
| 3,222,252 | 12/1965 | Kraus | 424/365 |
| 3,849,569 | 11/1974 | Mead | 424/271 |

FOREIGN PATENTS OR APPLICATIONS

| | | |
|---|---|---|
| 1,110,875 | 4/1968 | United Kingdom |
| 967,890 | 8/1964 | United Kingdom |
| 1,030,759 | 5/1966 | United Kingdom |

*Primary Examiner*—Sam Rosen
*Attorney, Agent, or Firm*—William G. Jameson; Sidney B. Williams, Jr.; Roman Saliwanchik

[57] ABSTRACT

Compositions and methods for treating mastitis in milk animals which comprises administering by intramammary infusion an effective amount of an anti-mastitis medicament dispersed in a vehicle comprising an oil, a fatty acid ester and, optionally, a fatty acid salt.

51 Claims, No Drawings

COMPOSITIONS AND METHOD FOR TREATING MASTITIS IN MILK ANIMALS

CROSS REFERENCE TO RELATED APPLICATIONS

This application is a continuation-in-part of my co-pending application Ser. No. 456,030 filed Mar. 29, 1974 now abandoned.

BACKGROUND OF THE INVENTION

Mastitis is an inflammatory condition of the mammary gland. It may affect any species, but bovine mastitis is of the greatest economic importance.

Bovine mastitis is usually associated with one or more microorganisms such as *Streptococcus agalactiae, Streptococcus dysgalactiae, Staphylococcus aureus, Aerobacter aerogenes, Escherichia coli, Pseudomonas aeruginosa, Salmonella enteritidis, Clostridium perfingens*, and *Corynebacterium pyogenes* which invade the udder through the teat canal and produce inflammation of the milk-producing tissue causing the formation of scar tissue which, once formed, may cause a permanent reduction in the cow's milk production. An infection can also alter the composition, quantity, appearance and quality of the milk.

The etiology of mastitis makes control of the problem dependent upon the critical diagnosis of the specific microbial agent involved, the correction of faulty managerial practices and the judicious use of intramammary therapy.

BRIEF SUMMARY OF THE INVENTION

This invention relates to new mastitis compositions and to methods of treating mastitis in milk animals by intramammary infusion of an anti-mastitis medicament dispersed in a special vehicle providing a short anti-mastitis medicament milk-out time.

The vehicle of the present invention comprises an oil and from 0.5 to 5.0% by weight of said oil of a fatty acid ester of a member selected from the group consisting of glycerin, propylene glycol, mono- and dihydric alcohols of from one to twelve carbon atoms, inclusive, and polyethylene glycols having a molecular weight of between about 200 and about 6000, said fatty acid being selected from a group consisting of long chain saturated and unsaturated monocarboxylic acids having from twelve to twenty carbon atoms, inclusive, i.e., a fatty acid ester formed from a fatty acid selected from the group consisting of long chain saturated and unsaturated monocarboxylic acids having from twelve to twenty carbon atoms, inclusive, and a member selected from the group consisting of glycerin, propylene glycol, mono- and dihydric alcohols of from one to twelve carbon atoms, inclusive, and polyethylene glycols having a molecular weight of between about 200 and 6000. In addition to a fatty acid ester as described above, the vehicle of the present invention may optionally include from 0.02% to 0.50% by weight of said oil of a fatty acid salt of a member selected from the group consisting of sodium, potassium and lithium, said fatty acid being selected from a group consisting of long chain saturated and unsaturated monocarboxylic acids having from twelve to twenty carbon atoms, inclusive; i.e., a fatty acid salt formed from a fatty acid selected from the group consisting of long chain saturated and unsaturated monocarboxlyic acids having from twelve to twenty carbon atoms, inclusive, and a member selected from the group consisting of sodium, potassium and lithium.

DETAILED DESCRIPTION

The present invention relates to compositions and methods of treating mastitis in animals, particularly milk aninmals, by intramammary infusion. Milk animal is any animal which has mammary glands and is capable of milk production.

Although bovine mastitis is of the greatest economic importance and for convenience references herein will be directed essentially to such situations, it will be understood that the compositions and methods of the present invention are applicable to other milk animals as well.

The compositions and methods of the present invention can be particularly advantageous for the treatment of mastitis because of a short anti-mastitis medicament milk-out time, i.e., the amount of time required for an anti-mastitis medicament to clear the udder after the last intramammary infusion. This property of a short anti-mastitis medicament milk-out time is of importance since milk contaminated with many of the anti-mastitis medicaments cannot be used for human consumption or marketed for cheese production.

The nature of the vehicle, on anti-mastitis medicament milk-out times, has long been considered important in formulating mastitis infusion compositions.

Heretofore, anti-mastitis medicaments for intramammary infusion have commonly been dispersed in an oil medium such as mineral oil or a vegetable oil gelled with a trivalent metallic stearate such as aluminum monostearate, e.g., a peanut oil medium containing 3% of aluminum monostearate. A disadvantage with intramammary infusion compositions gelled with a trivalent metallic stearate, as described above, is that the penicillin milk-out time for such compositions is quite long.

It is therefore a principal object of this invention to provide compositions and methods for treating animal mastitis by intramammary infusions affording short anti-mastitis medicament milk-out times. The anti-mastitis medicament penicillin is of importance in the treatment of bovine mastitis caused by various microorganisms and a chief aspect of the present invention is to provide compositions and methods for treating animal mastitis by intramammary infusions affording a short penicillin milk-out time.

The term "anti-mastitis medicament", as used in the specification and claims, refers to any antimicrobial effective to treat mastitis. Illustrative of the anti-mastitis medicaments which can be utilized in the compositions of the present invention include penicillin, neomycin, novobiocin, lincomycin, dihydrostreptomycin, streptomycin, erythromycin, polymyxin, tetracycline, oxytetracycline, chlorotetracycline, clindamycin, nitrofurazone, cephalosporins, analogs and derivatives thereof, and their pharmaceutically acceptable salts. The amount of anti-mastitis medicament employed will, of course, vary depending upon the severity of the mastitis but, in general, those amounts which have heretofore been used for the treatment of mastitis are suitable.

The term "penicillin", as used in the specification and claims, refers to any natural or synthetic penicillin and their pharmaceutically acceptable salts effective to treat mastitis. A preferred penicillin of the present invention is procaine penicillin G.

The term "Tegin" as used in the specification and claims is a brand of glyceryl monostearate supplied by Inolex Personal Care Division, Wilson Pharmaceutical and Chemical Corporation, 3 Science Road, Glenwood, Ill. 60425 and prepared from edible grade hydrogenated oil. Potassium hydroxide and stearic acid are employed in the esterification process so the finished product contains 8–10% potassium stearate.

In accordance with a specific feature of this invention, the oil of the vehicle may be any vegetable oil which is suitable for carrying an anti-mastitis medicament and which has been found fully acceptable for intramammary infusion. Vegetable oils may be generally classified as non-drying, semi-drying and drying oils. Drying vegetable oils include linseed oil and safflower oil. The drying properties of this group of oils is caused by the presence of unsaturated fatty acids in the oil. The degree of unsaturated fatty acids present can be expressed by the iodine value of the oil. Arranged according to their iodine value, the aforementioned drying vegetable oils are as follows:

| Linseed oil | not less than 170 |
|---|---|
| Safflower oil | 140 – 150 |

The class of semi-drying vegetable oils includes the following, arranged according to their iodine value.

| Soybean oil | 127 – 138 |
|---|---|
| Cottonseed oil | 105 – 114 |
| Sesame oil | 103 – 122 |
| Corn oil | 109 – 133 |

The class of non-drying vegetable oils includes the following, arranged according to their iodine value:

| Olive oil | 79 – 90 |
|---|---|
| Peanut oil | 84 – 102 |

As stated, vegetable oils are suitable for the vehicle, examples being peanut oil, sesame oil, corn oil, cottonseed oil, soybean oil, olive oil, and like vegetable oils or mixtures thereof. In a broader aspect, it is conceived that other oils may be employed, in part or in whole, for example, mineral oil. However, in such compositions, the milk-out specifications may require that the milk be completely clear of such oil in order to be available for human consumption.

The term "mineral oil" as used in the specification and claims refers to mixtures of liquid hydrocarbons known in medicine as liquid paraffin and light liquid paraffin or petroleum, for example, those of the United States or British Pharmacopeias.

An oil, i.e., a vegetable oil or a mineral oil, is transformed to a gel before being incorporated into the compositions of the present invention. This gelling is effected by treatment of the oil with a fatty acid ester of a member selected from the group consisting of glycerin, propylene glycol, mono- and dihydric alcohols of from one to twelve carbon atoms, inclusive, and polyethylene glycols having a molecular weight of between about 200 and about 6000, said fatty acid being selected from a group consisting of long chain saturated and unsaturated monocarboxylic acids having from twelve to twenty carbon atoms, inclusive. A fatty acid ester of the present invention which can be used is glyceryl monostearate.

The amount of glyceryl monostearate or other fatty acid ester which can be used in accordance with this invention is generally within the range of between about 0.5 and 5.0% by weight of the oil, and preferably from 1.0 to 4.0% by weight of the oil. A gel formed by gelling peanut oil with 2.0% by weight of glyceryl monostearate can be used as a vehicle for the preparation of compositions of this invention.

The vehicle of the present invention can also include a fatty acid salt of a member selected from the group consisting of sodium potassium and lithium, said fatty acid being selected from a group consisting of long chain saturated and unsaturated monocarboxylic acids having from twelve to twenty carbon atoms, inclusive. A fatty acid salt of the present invention which can be used is potassium stearate.

The amount of potassium stearate or other fatty acid salt which can be used in accordance with this invention is within the range of between about 0.02% and 0.15% by weight of the oil. However, this range can be from about 0.02% to 0.5% by weight of the oil. A gel formed by gelling peanut oil with 2.0% by weight of glyceryl monostearate and from about 0.16% to about 0.20% by weight of potassium stearate can be used as a vehicle for the preparation of the compositions of this invention.

To gel a mineral oil or a vegetable oil, the oil is heated to a suitable temperature which may vary somewhat with different oils but which will generally be below 100° C. Peanut oil, for example, can be gelled by heating it to 60°–90° C. and adding 2.0% by weight of glyceryl monostearate, and then cooling to 25° C. with stirring. There is no great danger in overheating, provided decomposition of the oil is not engendered. Heated oils can be gelled with a fatty acid ester.

The method of treating mastitis in accordance with the present invention involves administering to the affected mammary gland by intramammary infusion a composition as herein described.

The following examples are illustrative of the best mode contemplated by the inventor for carrying out his invention and are not to be construed as limiting.

EXAMPLE 1

One hundred grams of a composition for the treatment of mastitis is prepared from the following types and amounts of ingredients:

| Procaine Penicillin G | 500,000 Units |
|---|---|
| Sodium Novobiocin | 1.00 gram |
| Glyceryl monostearate | 1.00 gram |
| Peanut oil, q.s. | 100 grams |

Heat the peanut oil to 60°–90° C. and add the glyceryl monostearate, cool to 25° C. with stirring. Add the sodium novobiocin and procaine penicillin G with stirring and pass the product through a colloid mill. Fill the milled product into disposable mastitis syringes in 10 gram doses.

The foregoing composition is useful for the treatment of bovine mastitis by intramammary infusion.

EXAMPLE 2

One hundred grams of a composition for the treatment of mastitis is prepared from the following types and amounts of ingredients:

| | | |
|---|---|---|
| Procaine Penicillin G | 1,500,000 | Units |
| Sodium Novobiocin | 1.500 | gram |
| Glyceryl monostearate | 1.425 | gram |
| Potassium stearate | 0.075 | gram |
| Peanut oil, q.s. | 100 | grams |

Heat the peanut oil to 60°–90° C. and add the glyceryl monostearate and potassium stearate, cool to 25° C. with stirring. Add the sodium novobiocin and procaine penicillin G with stirring and pass the product through a colloid mill. Fill the milled product into disposable mastitis syringes in 10 gram doses.

The foregoing composition is useful for the treatment of bovine mastitis by intramammary infusion.

EXAMPLE 3

One hundred grams of a composition for the treatment of mastitis is prepared from the following types and amounts of ingredients:

| | | |
|---|---|---|
| Lincomycin hydrochloride | 2.0 | grams |
| Glyceryl monostearate | 2.0 | grams |
| Peanut oil, q.s. | 100 | grams |

Heat the peanut oil to 60°–90° C. with stirring. Add the lincomycin hydrochloride with stirring and pass the product through a colloid mill. Fill the milled product into disposable mastitis syringes in 10 gram doses.

The foregoing composition is useful for the treatment of bovine mastitis by intramammary infusion.

EXAMPLE 4

One hundred grams of a composition for the treatment of mastitis is prepared from the following types and amounts of ingredients:

| | | |
|---|---|---|
| Procaine Penicillin G | 500,000 | units |
| Sodium Novobiocin | 1.00 | gram |
| Glyceryl monostearate | 1.00 | gram |
| Mineral oil, q.s. | 100 | grams |

Heat the mineral oil to 60°–90° C. and add the glyceryl monostearate, cool to 25° C. with stirring. Add the procaine penicillin G and sodium novobiocin with stirring and pass the product through a colloid mill. Fill the milled product into disposable mastitis syringes in 10 gram doses.

The foregoing composition is useful for the treatment of bovine mastitis by intramammary infusion.

EXAMPLE 5

A composition for the treatment of mastitis is prepared from the following types and amounts of ingredients:

Part I:

| | | |
|---|---|---|
| Tegin | 15.140 | Kg. |
| Peanut oil U.S.P., q.s. ad | 757 | Liters |

Caution

Prevent contact with water or moist atmosphere.
Avoid contact with copper or brass.

Directions

Transfer 741 liters peanut oil to a suitable jacketed tank. Heat to 55°–60° C. (131°–140° F.) while mixing. Add all the Tegin slowly. Continue mixing until 80° C. (176° F.) is reached. Hold temperature at 80° C. for 30 minutes. Then begin cooling with cold $H_2O$ at a rate of 86 LPM rotometer reading. Continue cooling with mixing until 24°–25° C. (75° F.) is reached. Stop cooling system, drain jacket, and continue mixing for a minimum of 17 hours.

Part II:

| | | |
|---|---|---|
| Chlorobutanol USP Anhydrous (Excess 5%) | 3.974 | Kg. |
| [1]Procaine Penicillin G, U.S.P. Sterile Micronized (Excess 10%) | 8.327 | Kg. |
| [2]Sodium Novobiocin N.F. Micronized (Excess 10%) | | |
| Part I, q.s. ad | 757 | Liters |

[1]Standard = 1000 U/mg.
[2]Used on basis of assay to yield 165 mg. of novobiocin activity for a label claim of 150 mg. per 10 ml.

Caution

Avoid exposure to copper and brass protect from light and moist atmosphere.

Directions

Dissolve the chlorobutanol in approximately 700 liters of Part I. Mix a minimum of one hour using a twin blade stainless steel agitator in a glass lined or stainless steel tank. With constant stirring, add the procaine penicillin G and the sodium novobiocin. Mix thoroughly. Process through a Colloid Mill set at approximately 0.006 inch and discharge into a glass lined or stainless steel tank through a 60 mesh stainless steel screen. Wash Colloid Mill with Part I and q.s. ad 757 liters at room temperature. Mix thoroughly and fill the product into disposable mastitis syringes in 10 ml. doses. The foregoing composition is useful for the treatment of bovine mastitis by the intramammary infusion of 10 milliliters of said composition in each infected quarter after milking.

EXAMPLE 6

A composition for the treatment of mastitis is prepared from the following types and amounts of ingredients:

Part I:

| | | |
|---|---|---|
| Tegin | 2.5 | Kg. |
| Peanut oil U.S.P. | 500 | Kg. |

Caution

Prevent contact with water or moist atmosphere.
Avoid contact with copper or brass.

Directions

Transfer the peanut oil to a suitable jacketed tank. Heat to 55°–60° C. (131°–140° F.) while mixing. Add all the Tegin slowly. Continue mixing until 80° C. (176° F.) is reached. Hold temperature at 80° C. for 30 minutes. Then begin cooling with cold $H_2O$ at a rate of 86 LPM rotometer reading. Continue cooling with mixing until 24°–25° C. (75° F.) is reached. Stop cooling system, drain jacket, and continue mixing for a minimum of 17 hours.

| Part II: | | |
|---|---|---|
| Chlorobutanol U.S.P. Anhydrous | 2.3 | Kg. |
| ³Procaine Penicillin G. U.S.P. Sterile Micronized | 4.6 | Kg. |
| Part I, q.s. ad | 500 | Kg. |

³Standard = 1000 U/mg.
Use on basis to yield 100,000 U per 10 ml.

Caution

Avoid exposure to copper and brass protect from light and moist atmosphere.

Directions

Dissolve the chlorobutanol in approximately 450 kg. of Part I. Mix one hour using a twin blade stainless steel agitator in a glass lined or stainless steel tank. With constant stirring, add the procaine penicillin G. Mix thoroughly. Process through a Colloid Mill set at approximately 0.006 inch and discharge into a glass lined or stainless steel tank through a 60 mesh stainless steel screen. Wash Colloid Mill with Part I and q.s. ad 500 kg. at room temperature. Mix thoroughly and fill product into disposable mastitis syringes in 10 ml. doses.

The foregoing composition is useful for the treatment of bovine mastitis by intramammary infusion of 10 milliliters of said composition in each infested quarter after milking.

EXAMPLE 7

A composition for the treatment of mastitis is prepared from the following types and amounts of ingredients:

| Part I: | | |
|---|---|---|
| Tegin | 10 | Kg. |
| Peanut oil U.S.P. | 500 | Kg. |

Caution

Prevent contact with water or moist atmosphere. Avoid contact with copper or brass.

Directions

Transfer the peanut oil to a suitable jacketed tank. Heat to 55°–60° C. (131°–140° F.) while mixing. Add all the Tegin slowly. Continue mixing until 80° C. (176° F.) is reached. Hold temperature at 80° C. for 30 minutes. Then begin cooling with cold $H_2O$ at a rate of 86 LPM rotometer reading. Continue cooling with mixing until 24°–25° C. (75° F.) is reached. Stop cooling system, drain jacket, and continue mixing for a minimum of 17 hours.

| Part II: | | |
|---|---|---|
| Chlorobutanol U.S.P. Anhydrous | 2.3 | Kg. |
| ³Procaine Penicillin G. U.S.P. Sterile Micronized | 4.6 | Kg. |
| Part I, q.s. ad | 500 | Kg. |

³Standard = 1000 U/mg.
Use on basis to yield 100,000 U per 10 ml.

Caution

Avoid exposure to copper and brass protect from light and moist atmosphere.

Directions

Dissolve the chlorobutanol in approximately 450 kg. of Part I. Mix one hour using a twin blade stainless steel agitator in a glass lined or stainless steel tank. With constant stirring, add the procaine penicillin G. Mix thoroughly. Process through a Colloid Mill set at approximately 0.006 inch and discharge into a glass lined or stainless steel tank through a 60 mesh stainless steel screen. Wash Colloid Mill with Part I and q.s. ad 500 kg. at room temperature. Mix thoroughly and fill product into disposable mastitis syringes in 10 ml. doses.

The foregoing composition is useful for the treatment of bovine mastitis by intramammary infusion of 10 milliliters of said composition in each infested quarter after milking.

EXAMPLE 8

A composition for the treatment of mastitis is prepared from the following types and amounts of ingredients:

| Part I: | | |
|---|---|---|
| Tegin | 25 | Kg. |
| Peanut oil U.S.P. | 500 | Kg. |

Caution

Prevent contact with water or moist atmosphere. Avoid contact with copper or brass.

Directions

Transfer the peanut oil to a suitable jacketed tank. Heat to 55°–60° C. (131°–140° F.) while mixing. Add all the Tegin slowly. Continue mixing until 80° C. (176° F.) is reached. Hold temperature at 80° C. for 30 minutes. Then begin cooling with cold $H_2O$ at a rate of 86 LPM rotometer reading. Continue cooling with mixing until 24°–25° C. (75° F.) is reached. Stop cooling system, drain jacket, and continue mixing for a minimum of 17 hours.

| Part II: | | |
|---|---|---|
| Chlorobutanol U.S.P. Anhydrous | 2.3 | Kg. |
| ³Procaine Penicillin G. U.S.P. Sterile Micronized | 4.6 | Kg. |
| Part I, q.s. ad | 500 | Kg. |

³Standard = 1000 U/mg.
Use on basis to yield 100,000 U per 10 ml.

Caution

Avoid exposure to copper and brass protect from light and moist atmosphere.

Directions

Dissolve the chlorobutanol in approximately 450 kg. of Part I. Mix one hour using a twin blade stainless steel agitator in a glass lined or stainless steel tank. With constant stirring, add the procaine penicillin G. Mix thoroughly. Process through a Colloid Mill set at approximately 0.006 inch and discharge into a glass lined or stainless steel tank through a 60 mesh stainless steel screen. Wash Colloid Mill with Part I and q.s. ad 500 kg. at room temperature. Mix thoroughly and fill product into disposable mastitis syringes in 10 ml. doses.

The foregoing composition is useful for the treatment of bovine mastitis by intramammary infusion of 10 milliliters of said composition in each infested quarter after milking.

EXAMPLE 9

A composition for the treatment of mastitis is prepared from the following types and amounts of ingredients:

Part I:

| | | |
|---|---|---|
| Tegin | 5 | Kg. |
| Peanut Oil U.S.P. | 500 | Kg. |

Caution

Prevent contact with water or moist atmosphere. Avoid contact with copper or brass.

Directions

Transfer the peanut oil to a suitable jacketed tank. Heat to 55°–60° C. (131°–140° F.) while mixing. Add all the Tegin slowly. Continue mixing until 80° C. (176° F.) is reached. Hold temperature at 80° C. for 30 minutes. Then begin cooling with cold $H_2O$ at a rate of 86 LPM rotometer reading. Continue cooling with mixing until 24°–25° C. (75° F.) is reached. Stop cooling system, drain jacket, and continue mixing for a minimum of 17 hours.

| Part II: | | |
|---|---|---|
| Chlorobutanol U.S.P. Anhydrous | 2.3 | Kg. |
| ³Procaine Penicillin G. U.S.P. | | |
| Sterile Micronized | 4.6 | Kg. |
| Part I, q.s. ad | 500 | Kg. |

³Standard = 1000 U/mg.
Use on basis to yield 100,000 U per 10 ml.

Caution

Avoid exposure to copper and brass protect from light and moist atmosphere.

Directions

Dissolve the chlorobutanol in approximately 450 kg. of Part I. Mix one hour using a twin blade stainless steal agitator in a glass lined or stainless steel tank. With constant stirring, add the procaine penicillin G. Mix thoroughly. Process through a Colloid Mill set at approximately 0.006 inch and discharge into a glass lined or stainless steel tank through a 60 mesh stainless steel screen. Wash Colloid Mill with Part I and q.s. ad 500 kg. at room temperature. Mix thoroughly and fill product into disposable mastitis syringes in 10 ml. doses.

The foregoing composition is useful for the treatment of bovine mastitis by intramammary infusion of 10 milliliters of said composition in each infested quarter after milking.

I claim:

1. A method of treating mastitis in milk animals which comprises administering to the affected mammary region by intramammary infusion a composition which comprises an effective amount of an anti-mastitis medicament dispersed in a gelled vehicle for carrying said anti-mastitis medicament comprising a vegetable oil acceptable for intramammary infusion selected from the group consisting of non-drying, semi-drying, and drying oils and blends thereof; and from about 0.5% to 5.0% by weight of said oil of a fatty acid ester formed from a fatty acid selected from the group consisting of long chain saturated and unsaturated monocarboxylic acids having from twelve to twenty carbon atoms, inclusive, and a member selected from the group consisting of glycerin, propylene glycol, mono- and dihydric alcohols of from one to twelve carbon atoms, inclusive, and polyethylene glycols having a molecular weight of between about 200 and about 6000.

2. The method as defined in claim 1 in which the vegetable oil is peanut oil.

3. The method as defined in claim 1 in which the fatty acid ester is glyceryl monostearate.

4. The method as defined in claim 1 in which the vegetable oil is peanut oil and the fatty acid ester is glyceryl monostearate.

5. The method as defined in claim 4 in which the glyceryl monostearate is present in an amount of about 2% by weight of said oil.

6. The method as defined in claim 1 in which the vegetable oil is peanut oil, the fatty acid ester is glyceryl monostearate and the anti-mastitis medicament is penicillin.

7. The method as defined in claim 6 in which the glyceryl monostearate is present in an amount of about 2% by weight of said oil.

8. The method as defined in claim 1 in which said vehicle, in addition, contains from about 0.02% to 0.50% by weight of said oil of a fatty acid salt formed from a fatty acid selected from the group consisting of long chain saturated and unsaturated monocarboxylic acids having from twelve to twenty carbon atoms, inclusive, and a member selected from the group consisting of sodium, potassium and lithium.

9. The method as defined in claim 8 in which the vegetable oil is peanut oil.

10. The method as defined in claim 8 in which the fatty acid ester is glyceryl monostearate.

11. The method as defined in claim 8 in which the fatty acid salt is potassium stearate.

12. The method as defined in claim 8 in which the vegetable oil is peanut oil, the fatty acid ester is glyceryl monostearate and the fatty acid salt is potassium stearate.

13. The method as defined in claim 12 in which the potassium stearate is present in an amount of from about 0.02% to 0.15% by weight of said oil.

14. The method as defined in claim 8 in which the vegetable oil is peanut oil, the fatty acid ester is glyceryl monostearate, the fatty acid salt is potassium stearate, and the anti-mastitis medicament is penicillin.

15. The method as defined in claim 14 in which the glyceryl monostearate is present in an amount of about 2% by weight of said oil and the potassium stearate is present in an amount of from about 0.16% to about 0.20% by weight of said oil.

16. A composition for treating mastitis in milk animals by intramammary infusion which comprises an effective amount of an anti-mastitis medicament dispersed in a gelled vehicle for carrying said anti-mastitis medicament comprising a vegetable oil acceptable for intramammary infusion selected from the group consisting of non-drying, semi-drying, and drying oils and blends of non-drying oils and an oil selected from the group consisting of semi-drying and drying oils; and from about 0.5% to 5.0% by weight of said oil of a fatty acid ester formed from a fatty acid selected from the group consisting of long chain saturated and unsaturated monocarboxylic acids having from twelve to twenty carbon atoms, inclusive, and a member selected from the group consisting of glycerin, propylene glycol, mono- and dihydric alcohols of from one to twelve carbon atoms, inclusive, and polyethylene glycols having a molecular weight of between about 200 and about 6000.

17. The composition as defined in claim 16 in which the vegetable oil is peanut oil.

18. The composition as defined in claim 16 in which the fatty acid ester is glyceryl monostearate.

19. The composition as defined in claim 16 in which the vegetable oil is peanut oil and the fatty acid ester is glyceryl monostearate.

20. The composition as defined in claim 19 in which the glyceryl monostearate is present in an amount of about 2% by weight of said oil.

21. The composition as defined in claim 16 in which the vegetable oil is peanut oil, the fatty acid ester is glyceryl monostearate and the anti-mastitis medicament is penicillin.

22. The composition as defined in claim 21 in which the glyceryl monostearate is present in an amount of about 2% by weight of said oil.

23. A composition as defined in claim 16 in which said vehicle, in addition, contains from about 0.02% to 0.50% by weight of said oil of a fatty acid salt formed from a fatty acid selected from the group consisting of long chain saturated and unsaturated monocarboxylic acids having from twelve to twenty carbon atoms, inclusive, and a member selected from the group consisting of sodium potassium and lithium.

24. The composition as defined in claim 23 in which the fatty acid ester is glyceryl monostearate.

25. The composition as defined in claim 23 in which the fatty acid salt is potassium stearate.

26. The composition as defined in claim 23 in which the vegetable oil is peanut oil, the fatty acid ester is glyceryl monostearate and the fatty acid salt is potassium stearate.

27. The composition as defined in claim 26 in which the potassium stearate is present in an amount of from about 0.02% to 0.15% by weight of said oil.

28. The composition as defined in claim 23 in which the vegetable oil is peanut oil, the fatty acid ester is glyceryl monostearate, the fatty acid ester is potassium stearate, and the anti-mastitis medicament is penicillin.

29. The composition as defined in claim 28 in which the glyceryl monostearate is present in an amount of about 2% by weight of said oil and the potassium stearate is present in an amount of from about 0.16% to about 0.20% by weight of said oil.

30. A method of treating mastitis in milk animals which comprises administering to the affected mammary region by intramammary infusion a composition which comprises an effective amount of an anti-mastitis medicament dispersed in a gelled vehicle for carrying said anti-mastitis medicament comprising a mineral oil and from about 0.5% to 5.0% by weight of said oil of a fatty acid ester formed from a fatty acid selected from the group consisting of long chain saturated and unsaturated monocarboxylic acids having from twelve to twenty carbon atoms, inclusive, and a member selected from the group consisting of glycerin, propylene glycol, mono- and dihydric alcohols of from one to twelve carbon atoms, inclusive, and polyethylene glycols having a molecular weight of between about 200 and about 6000.

31. The method as defined in claim 30 in which said vehicle, in addition, contains from about 0.02% to 0.50% by weight of said oil of a fatty acid salt formed from a fatty acid selected from the group consisting of long chain saturated and unsaturated monocarboxylic acids having from twelve to twenty carbon atoms, inclusive, and a member selected from the group consisting of sodium, potassium and lithium.

32. A method for reducing the amount of time required for an anti-mastitis medicament to clear the udder of a milk animal after the last intramammary infusion of said anti-mastitis medicament which comprises administering by intramammary infusion an effective amount of an anti-mastitis medicament dispersed in a gelled vehicle for carrying said anti-mastitis medicament which comprises:
  a. a vegetable oil acceptable for intramammary infusion selected from the group consisting of non-drying, semi-drying, and drying oils and blends thereof; and
  b. from about 0.5% to 5.0% by weight of a fatty acid ester formed from a fatty acid selected from the group consisting of long chain saturated and unsaturated monocarboxlyic acids having from twelve to twenty carbon atoms, inclusive, and a member selected from the group consisting of glycerin, propylene glycol, mono- and dihydric alcohols of from one to twelve carbon atoms, inclusive, and polyethylene glycols having a molecular weight of between about 200 and about 6000.

33. The method as defined claim claim 32 in which the anti-mastitis medicament is penicillin.

34. The method as defined in claim 32 in which said vehicle, in addition, contains from about 0.02% to 0.50% by weight of said oil of a fatty acid salt formed from a fatty acid selected from the group consisting of long chain saturated and unsaturated monocarboxylic acids having from twelve to twenty carbon atoms, inclusive, and a member selected from the group consisting of sodium potassium and lithium.

35. The method as defined in claim 34 in which the anti-mastitis medicament is penicillin.

36. A method for reducing the amount of time required for an anti-mastitis medicament to clear the udder of a milk animal after the last intramammary infusion of said anti-mastitis medicament which comprises administering by intramammary infusion an effective amount of an anti-mastitis medicament dispersed in a gelled vehicle for carrying said anti-mastitis medicament which comprises:
  a. a mineral oil; and
  b. from about 0.5% to 5.0% by weight of a fatty acid ester formed from a fatty acid selected from the group consisting of long chain saturated and unsaturated monocarboxylic acids having from twelve to twenty carbon atoms, inclusive, and a member selected from the group consisting of glycerin, propylene glycol, mono- and dihydric alcohols of from one to twelve carbon atoms, inclusive, and polyethylene glycols having a molecular weight of between about 200 and about 6000.

37. The method as defined in claim 36 in which said vehicle, in addition, contains from about 0.02% to 0.50% by weight of said oil of a fatty acid salt formed from a fatty acid selected from the group consisting of long chain saturated and unsaturated monocarboxylic acids having from twelve to twenty carbon atoms, inclusive, and a member selected from the group consisting of sodium, potassium and lithium.

38. A method of treating mastitis in milk animals which comprises administering to the affected mammary region by intramammary infusion a composition which comprises an effective amount of an anti-mastitis medicament dispersed in a vehicle for carrying said anti-mastitis medicament comprising a vegetable oil acceptable for intramammary infusion selected from the group consisting of non-drying, semi-drying, and drying oils and blends thereof; gelled with from about 0.5% to 5.0% by weight of said oil of Tegin.

39. The method as defined in claim 38 in which the vegetable oil is peanut oil.

40. The method as defined in claim 39 in which the Tegin is present in an amount of about 2% by weight of said oil.

41. The method as defined in claim 39 in which the anti-mastitis medicament is penicillin.

42. The method as defined in claim 41 in which the Tegin is present in an amount of about 2% by weight of said oil.

43. The method as defined in claim 39 in which the anti-mastitis medicament is procaine penicillin G.

44. The method as defined in claim 43 in which the Tegin is present in an amount of about 2% by weight of said oil.

45. A composition for treating mastitis in milk animals by intramammary infusion which comprises an effective amount of an anti-mastitis medicament dispersed in a vehicle for carrying said anti-mastitis medicament comprising a vegetable oil acceptable for intramammary infusion selected from the group consisting of non-drying, semi-drying, and drying oils and blends of non-drying oils and an oil selected from the group consisting of semi-drying and drying oils; gelled with from about 0.5% to 5.0% by weight of said oil of Tegin.

46. The composition as defined in claim 45 in which the vegetable oil is peanut oil.

47. The composition as defined in claim 46 in which the Tegin is present in an amount of about 2% by weight of said oil.

48. The composition as defined in claim 46 in which the anti-mastitis medicament is penicillin.

49. The composition as defined in claim 48 in which the Tegin is present in an amount of about 2% by weight of said oil.

50. The composition as defined in claim 46 in which the anti-mastitis medicament is procaine penicillin G.

51. The composition as defined in claim 50 in which the Tegin is present in an amount of about 2% by weight of said oil.

* * * * *